United States Patent [19]

Houck et al.

[11] Patent Number: 4,943,674
[45] Date of Patent: Jul. 24, 1990

[54] FRUIT SPECIFIC TRANSCRIPTIONAL FACTORS

[75] Inventors: Catherine M. Houck, Vacaville; Julie R. Pear, Davis, both of Calif.

[73] Assignee: Calgene, Inc., Davis, Calif.

[21] Appl. No.: 54,369

[22] Filed: May 26, 1987

[51] Int. Cl.[5] .................. A01H 1/04; C12N 15/00; C12N 5/00; C07H 15/12

[52] U.S. Cl. .................. 800/205; 435/172.3; 435/320; 435/240.4; 536/27; 935/35; 935/64; 935/67; 800/DIG. 44

[58] Field of Search ............ 536/27; 435/172.3, 240.4, 435/320; 800/1

[56] References Cited

PUBLICATIONS

Goodman et al., 1987, Science 236: 48–54.
Faccioth et al., 1985, Biotechnol. 3(3): 241–246.
Sengupta-Gopalan et al., 1985, Proc. Natl. Acad. Sci. USA 82: 3320–3324.
Zhang-Liang Chen, Mary A. Schuler & Roger N. Beachy Functional Analysis of Regulatory Elements in a Plant Embryo-Specific Gene Proc. Natl. Acad. Sci. USA, (1986) 83: 8560–8564.
R. N. Beachy, Z.-L. Chen, R. B. Horsch, S. G. Rogers, N. J. Hoffman & R. T. Fraley, Accumulation and Assembly of soybean $\beta$-Conglycinin in Seeds of Transformed Petunia Plants, The EMBO Journal, (1985) 4(12): 3047–3053.
Peter Ueng, Gad Galili, Victoria Sapanara, Peter B. Goldsbrough, Phillip Dube, Roger N. Beachy & Brian A. Larkins, Expression of a Maize Storage Protein Gene in Petunia Plants is not Restricted to Seeds, Plant Physiol. (1988) 86: 1281–1285.
Boston et al., Expression from Heterologous Promoters in Electroporated Carrot Protoplasts, *Plant Physiol,* (1987)83:742–746.
Mansson et al., Characterization of Fruit Specific cDNAs from Tomato, *Mol Gen Genet,* (1985)200:356–361.
Sengupta-Gopalan et al., Developmentally regulated expression of the bean $\beta$-Phaseolin gene in Tobacco Seed, *Proc. Natl. Acad. Sci. USA,* (1985)82:3320–3324.

Primary Examiner—Charles F. Warren
Assistant Examiner—David T. Fox
Attorney, Agent, or Firm—Barbara Rae-Venter

[57] ABSTRACT

Fruit specific regulatory regions are identified employing cDNA screening. The resulting fruit specific regulatory regions are manipulated for use with foreign sequences for introduction into plant cells to provide transformed plants having fruit with a modified phenotypic property. The invention is exemplified with a tomato fruit specific promoter which is active throughout the stages of fruit ripening.

14 Claims, 4 Drawing Sheets

```
5
    GENOMIC  CATTAAAATCTTATCTGACCTATAAAATAAATTATTTGCTCAACTCAAAATAGTTTTTCATTTCTAAA
    GENOMIC  ATTAGTATAATTATTAGTGAATATTTAATTAACATAATTGTATACTAAGGGGCCTATAAATTGGATTC
    CDNA                                CAACTTTCTTCTTCTGCTCATCAATTAGCAATTAATCCAAA
    GENOMIC  TTCTCAAAGAAAAATAAAATCACCAGACAACTTTCTTCTTCTGCTCATCAATT

10  CDNA     ACCATTATGGCTGCCAAAAATTCAGAGATGAAGTTTGCTATCTTCTTCGTTGTTCTTTTGACGACCACT
                 METAlaAlaLysAsnSerGluMETLysPheAlaIlePhePheValValLeuLeuThrThrThr
    CDNA     TT
    GENOMIC  ------------(INTRON 500-800 bp)------------------------TATCTATAGTTT
                 Le
    GENOMIC  GCTTCTAATGATTCATAGCTATATATTTGGAGAGGAGAGAGACAAACGATATTAAGAAAGGGAGGAGAG
15  GENOMIC  AGGCGAGGTAAATCTGAAATAGAGAAGAGAAAGGCAACCAATTTTGATCATCTATCATACTTTTGATTA
    GENOMIC  TTATTTTTATTATATGTACGTTTACATTACAGTTTTCGAATTCTTACATTAATCTTAATCATAATATAT
    CDNA     --AGTTGATATGTCTGGAATTTCGAAAATGCAAGTGATGGCTCTTCGAGACATACCCCCACAAGAAACA
    GENOMIC  ACAGTTGATATGTCTGGAATTTCGAAAATGCAAGTGATGGCTCTTCGAGACATACCCCCACAAGAAACA
                 uValAspMETSerGlyIleSerLysLysMETGlnValMETAlaLeuArgAspIleProProGlnGluThr
    CDNA     TTGCTGAAAATGAAGCTACTTCCCACAAATATTTTGGGACTTTGTAACGAACCTTGCAGCTCAAACTCT
20  GENOMIC  TTGCTGAAAATGAAGCTACTTCCCACAAATATTTTGGGACTTTGTAACGAACCTTGCAGCTCAAACTCT
                 LeuLeuLysMETLysLeuLeuProThrAsnIleLeuGlyLeuCysAsnGluProCysSerSerAsnSer
```

FIG.1-1

```
GENOMIC   CATTAAAAATCTTATCTGACCTATAAAATAATTATTGCTCAACTCAAAATAGTTTTCATTTCTAAA

GENOMIC   ATTAGTATAATTATTAGTGAATATTTAATTAACATAATTGTATACTAAGGGCCTATAAATTGGATTC

CDNA                      CAACTTTCTTCTTCTGCTCATCAATTAGCAATTAATCCAAA
GENOMIC   TTCTCAAAGAAAATAAAATCACCAGACAACTTTCTTCTTCTGCTCATCAATT

CDNA      ACCATTATGGCTGCCAAAAATTCAGAGATGAAGTTTGCTATCTTCTTCGTTGTTCTTTTGACGACCACT
GENOMIC              METAlaAlaLysAsnSerGluMETLysPheAlaIlePheValValLeuLeuThrThrThr

CDNA      TT
GENOMIC   --------(INTRON 500-800 bp)--------------TATCTATAGTTT
          Le

GENOMIC   GCTTCTAATGATTCATAGCTATATATTTGGAGAGAGAGAGACAAACGATATTAAGAAAGGGAGGAGAG

GENOMIC   AGGCGAGGTAAATCTGAAATAGAAGAAGAAAGGCAACCAATTTGATCATCTATCATACTTTGATTA

GENOMIC   TTATTTTATTATATGTACGTTTACATTACAGTTTTCGAATTCTTACATTAATCTTAATCATATATAT

CDNA        --AGTTGATATGTCTGGAATTTCGAAAATGCAAGTGATGGCTCTTCGAGACATACCCCCACAAGAAACA
GENOMIC   ACAGTTGATATGTCTGGAATTTCGAAAATGCAAGTGATGGCTCTTCGAGACATACCCCCACAAGAAACA
            uValAspMETSerGlyIleSerLysMETGlnValMETAlaLeuArgAspIleProProGlnGluThr

CDNA      TTGCTGAAAATGAAGCTACTTCCCACAAATATTTGGGACTTTGTAACGAACCTTGCAGCTCAAACTCT
GENOMIC   TTGCTGAAAATGAAGCTACTTCCCACAAATATTTGGGACTTTGTAACGAACCTTGCAGCTCAAACTCT
          LeuLeuLysMETLysLeuLeuProThrAsnIleLeuGlyLeuCysAsnGluProCysSerSerAsnSer
```

```
CDNA      GATTGCATCGGAATTACCCTTTGCCAATTTTGTAAGGAGAAGACGGACCAGTATGGTTTAACATACCGT
GENOMIC   GATTGCATCGGAATTACCCTTTGCCAATTTTGTAAGGAGAAGACGGACCAGTATGGTTTAACATACCGT
          AspCysIleGlyIleThrLeuCysGlnPheCysLysLysGluLysThrAspGlnTyrGlyLeuThrTyrArg

CDNA      ACATGCAACCTGTGCCTTGAACAATATCAATGATCTATCGATCTATCGATCTATTATCTGTCT
25 GENOMIC ACATGCAACCTGTGCCTTGAACAATATCAATGATCTATCGATCTATCGATCTATTATCTGTCT
          ThrCysAsnLeuLeuPro

CDNA      CTGCGCGTATAGTGTTGTCTGTACCTTTGGTGTGAAGAATAAAGGGATACATATATCTAGATA
GENOMIC   CTGCGCGTATAGTGTTGTCTGTACCTTTGGTGTGAAGAATAAAGGGATACATATATCTAGATA

CDNA      TATTCTAGGTAATGTCCTATTGTATTTAAAATTTGTAGCAATGATTGTTTGAATAAAAACATACCATGA
GENOMIC   TATTCTAGGTAATGTCCTATTGTATTTAAAATTTGTAGCAATGATTGTTTGAATAAAAACATACCATGA

CDNA      GTGAAATAATTATTCCACATTAATTCACGTATTTATTCACTTATGATACGTATTTTGTTCCTTTCGC
GENOMIC   GTGAAATAATTATTCCACATTAATTCACGTATTTATTCACTTATGATACGTATTTTGTTCCTTTCGC

CDNA      GT
GENOMIC   GTAGATT
35
```

| | |
|---|---|
| 2A11 | ⓋM A L R D I P P Q E T L L |
| PA1b | ⓋC S P F D I P P C G S P L C R C I |
| Chick pea inhibitor | ⓋC T - K S I P P - - - - Q C R C N |
| Lima bean inhibitor | L C T - K S I P P - - - - Q C R C T |
| α₁-antitrypsin | L G A I P M S I P P E V |

FIG. 2-2

| | |
|---|---|
| 2A11 | T N I L G L C N E P C S S N S D C I |
| PA1b | G S P L C R C I P A G L V I G N C R |
| Barley chloroform/methanol-soluble protein d | T N L L G N C R - F Y L V Q Q T C A |
| Wheat α-amylase inhibitor 0.28 | V S A L T G C R - A M V K L Q C V |
| Wheat albumin | V P A L P A C R P L - L R L Q - C N |
| Millet bi-functional inhibitor | N N P L D S C R W Y VS_A T_K R -T_A C G |
| Castor bean 2S small subunit | Q Q N L R Q C Q E Y I K Q Q V S G Q |
| Napin small subunit | A Q N L R A C Q Q W L N K Q A M Q S |

FRUIT SPECIFIC TRANSCRIPTIONAL FACTORS

INTRODUCTION

1. Technical Field

This invention relates to DNA expression cassettes capable of directing fruit-specific expression of in vitro constructed expression cassettes in plants. The invention is exemplified by promoters useful in fruit-specific transcription in a tomato plant.

2. Background

In manipulating plants, the situation has proven to be of much more difficulty than the efforts employed with prokaryote and mammalian hosts. As compared to prokaryotes and mammalian cells, much less was known about the biochemistry and cell biology of plant cells and plants. The ability to transform plant cells and regenerate plants is unique to flora since other differentiated species provide readily available transformable germ cells which may be fertilized and introduced into the live host for fetal development to a mature fetus. There has been substantial interest in modifying the ovum with inducible transcriptonal initiation regions to afford inducible transcription and expression of the gene introduced into the ovum, rather than constituitive expression which would result in expression throughout the fetus.

Also, for plants, it is frequently desirable to be able to control expression at a particular stage in the growth of the plant or in a particular plant part. During the various stages of the growth of the plant, and as to the various components of the plant, it will frequently be desirable to direct the effect of the construct introduced into the entire plant or a particular part and/or to a particular stage of differentiation of the plant cell. For this purpose, regulatory sequences are required which afford the desired initiation of transcription in the appropriate cell types and/or at the appropriate time in the plant development, without having serious detrimental effects on the plant development and productivity.

It is therefore important to be able to isolate sequences which can be manipulated to provide the desired regulation of transcription in a plant cell host during the growing cycle of the plant. One aspect of this interest is the ability to change the phenotype of fruit, so as to provide fruit which will have improved aspects for storage, handling, cooking, organoleptic properties, freezing, nutritional value, and the like.

3. Relevant Literature cDNA clones from tomato displaying differential expression during fruit development have been isolated and characterized (Mansson et al., *Mol. Gen. Genet.* (1985) 200: 356-361; Slater et al., *Plant Mol. Biol.* (1985) 5: 137-147). The studies have focused primarily on mRNAs which accumulate during fruit ripening. One of the proteins encoded by the ripening-specific cDNAs has been identified as polygalacturonase (Slater et al., Plant Mol. Biol. (1985) 5: 137-147). A cDNA clone which encodes tomator polygalacturonase has been sequenced. Grierson et al., *Nucleic Acids Research* (1986) 14: 8595-8603. The concentration of polygalacturonase mRNA increases 2000-fold between the immature-green and red-ripe stages of fruit development. This suggests that expression of the enzyme is regulated by the specific mRNA concentration which in turn is regulated by an increase in transcription. Della Penna et al., *Proc. Natl. Acad. Sci. (USA)* (1986) 83: 6420-6424.

Mature plastid mRNA for psbA (one of the components of photosystem II) reaches its highest level late in fruit development, whereas after the onset of ripening, plastid mRNAs for other components of photosystem I and II decline to nondetectable levels in chromoplasts. Piechulla et al., *Plant Molec. Biol.* (1986) 7: 367-376.

Other studies have focused on cDNAs encoding genes under inducible regulation, e.g. proteinase inhibitors which are expressed in response to wounding in tomato (Graham et al., *J. Biol. Chem.* (1985) 260: 6555-6560; Graham et al., *J. Biol. Chem.* (1985) 260: 6561-6564) and on mRNAs correlated with ethylene synthesis in ripening fruit and leaves after wounding. Smith et al., *Planta* (1986) 168: 94-100.

Leaf disc transformation of cultivated tomato is described by McCormick, et al., *Plant Cell Reports* (1986) 5: 81-89.

SUMMARY OF THE INVENTION

Novel DNA constructions are provided employing a "fruit-specific promoter," particularly one active beginning at or shortly after anthesis, joined to a DNA sequence of interest and a transcriptional termination region. A DNA construct may be introduced into a plant cell host for integration into the genome and transcription regulated at a time at or subsequent to anthesis. In this manner, high levels of RNA and, as appropriate, polypeptides, may be achieved during formation and ripening of fruit.

BRIEF DESCRIPTION OF THE DRAWINGS

FIG. 1 shows the DNA sequence for pCGN1298 ("Genomic") and pCGN1299 ("cDNA") and the amino acid sequence encoded by the two clones.

FIG. 2 shows a comparison of the 2A11 protein sequence to pea albumin 1b (PA1b) and a number of other low molecular weight abundant proteins from plants as indicated in the Figure.

DESCRIPTION OF THE SPECIFIC EMBODIMENTS

In accordance with the subject invention, DNA constructs are provided which allow for modification of plant phenotype during fruit maturation and ripening. The DNA constructs provide for a regulated transcriptional initiation region associated with fruit development and ripening, preferably a transcriptional initiation region which is active upon or shortly after anthesis. Downstream from and under the transcriptional initiation regulation of the fruit related initiation region will be a sequence of interest which will provide for modification of the phenotype of the fruit. Desirably, integration constructs may be prepared which allow for integration of the transcriptional cassette into the genome of a plant host. Conveniently, the vector may include a multiple cloning site downstream from the fruit related transcriptional initiation region, so that the integration construct may be employed for a variety of sequences in an efficient manner.

Of particular interest is a transcriptional initiation region activated at or shortly after anthesis, so that in the early development of the fruit, it provides the desired level of transcription of the sequence of interest. Normally, the sequence of interest will be involved in affecting the process in the early formation of the fruit or providing a property which is desirable during the growing (expansion) period of the fruit, or at or after harvesting. Desirably, the transcriptional initiation region maintains its activity during the expansion and maturation of the green fruit, more desirably continues active through the ripening or red fruit period. The ripening stages of the tomato may be broken down into mature green, breaker, turning, pink, light red and red. Comparable periods for other fruit are referred to as stages of ripening.

The transcriptional initiation region may be native or homologous to the host or foreign or heterologous to the host. By foreign is intended that the transcriptional initiation region is not found in the wild-type host into which the transcriptional initiation region is introduced. Of particular interest is a tomato fruit-specific transcriptional initiation region referred to as 2A11 and which regulates the expression of a 2A11 cDNA sequence described in the Experimental section. This transcriptional initiation region provides for an abutment messenger, being activated at or shortly after anthesis and remaining active until the red fruit stage. The expressed protein is a sulfur-rich protein similar to other plant storage proteins in sulfur content and size.

Other fruit-specific promoters may be activated at times subsequent to anthesis, such as prior to or during the green fruit stage, during pre-ripe (e.g., breaker) or even into the red fruit stage.

A transcriptional initiation region may be employed for varying the phenotype of the fruit. Various changes in phenotype are of interest. These changes may include up- or down-regulation of formation of a particular saccharide, involving mono- or polysaccharides, involving such enzymes as polygalacturonase, levansucrase, dextransucrase, invertase, etc. Other properties of interest for modification include response to stress, organisms, herbicides, bruising, mechanical agitation, etc., change in growth regulators, organoleptic properties, etc.

The transcriptional cassette will include in the 5'-3' direction of transcription, a transcriptional and translational initiation region, a sequence of interest, and a transcriptional and translational termination region functional in plants. One or more introns may be also be present. The DNA sequence may have any open reading frame encoding a peptide of interest, e.g. an enzyme, or a sequence complementary to a genomic sequence, where the genomic sequence may be an open reading frame, an intron, a non-coding leader sequence, or any other sequence where the complementary sequence will inhibit transcription, messenger RNA processing, e.g. splicing, or translation. The DNA sequence of interest may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest.

In preparing the transcription cassette, the various DNA fragments may be manipulated, so as to provide for the DNA sequences in the proper orientation and, as appropriate, in the proper reading frame. Toward this end, adapters or linkers may be employed for joining the DNA fragments or other manipulations may be involved to provide for convenient restriction sites, removal of superfluous DNA, removal of restriction sites, or the like. Toward this end, in vitro mutagenesis, primer repair, restriction, annealing, resection, ligation, or the like may be employed, where insertions, deletions or substitutions, e.g. transitions and transversions, may be involved.

The termination region which is employed will be primarily one of convenience, since the termination regions appear to be relatively interchangeable. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions.

By appropriate manipulations, such as restriction, chewing back or filling in overhangs to provide blunt ends, ligation of linkers, or the like, complementary ends of the fragments can be provided for joining and ligation.

In carrying out the various steps, cloning is employed, so as to amplify the amount of DNA and to allow for analyzing the DNA to ensure that the operations have occurred in proper manner. A wide variety of cloning vectors are available, where the cloning vector includes a replication system functional in *E. coli* and a marker which allows for selection of the transformed cells. Illustrative vectors include pBR322, pUC series, M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constucts may be cloned in the same or different plasmids.

In addition to the transcription construct, depending upon the manner of introduction of the transcription construct into the plant, other DNA sequences may be required. For example, when using the Ti- or Ri-plasmid for transformation of plant cells, as described below, at least the right border and frequently both the right and left borders of the T-DNA of the Ti- or Ri-plasmids will be joined as flanking regions to the transcription construct. The use of T-DNA for transformation of plant cells has received extensive study and is amply described in EPA Serial No. 120;516, Hoekema, In: The Binary Plant Vector System Offsetdrukkerij Kanters B. V., Alblasserdam, 1985, Chapter V Knauf, et al., Genetic Analysis of Host Range Expression by Agrobacterium, In: Molecular Genetics of the Bacteria-Plant Interaction, Puhler, A. ed., Springer-Verlag, NY, 1983, p. 245, and An et al., EMBO J. (1985) 4: 277–284.

Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated and avoid hopping.

The transcription construct will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced.

A variety of techniques are available for the introduction of DNA into a plant cell host. These techniques include transformation with Ti-DNA employing *A. tumefaciens* or *A. rhizogenes* as the transforming agent, protoplast fusion, injection, electroporation, etc. For transformation with Agrobacterium, plasmids can be prepared in *E. coli* which plasmids contain DNA homologous with the Ti-plasmid, particularly T-DNA. The plasmid may or may not be capable of replication in Agrobacterium, that is, it may or may not have a broad spectrum prokaryotic replication system, e.g., RK290, depending in part upon whether the transcription construct is to be integrated into the Ti-plasmid or be retained on an independent plasmid. By means of a helper plasmid, the transcription construct may be transferred to the *A. tumefaciens* and the resulting transformed organism used for transforming plant cells.

Conveniently, explants may be cultivated with the *A. tumefaciens* or *A. rhizogenes* to allow for transfer of the transcription construct to the plant cells, the plant cells dispersed in an appropriate selective medium for selection, grown to callus, shoots grown and plantlets regenerated from the callus by growing in rooting medium. The Agrobacterium host will contain a plasmid having the vir genes necessary for transfer of the T-DNA to the plant cells and may or may not have T-DNA. For injection and electroporation, disarmed Ti-plasmids (lacking the tumor genes, particularly the T-DNA region) may be introduced into the plant cell.

As a host cell, any of a number of fruit bearing plants may be employed in which the plant parts of interest are derived from the ovary wall. These include tree berries such as tomato, grape, blueberry, cranberry, currant, and eggplant; stone fruits (drupes) such as cherry, plum, apricot, peach, nectarine and avocado; compound fruits (druplets) such as raspberry and blackberry. In hesperidium (oranges, citrus), the expression cassette might be expected to be expressed in the "juicy" portion of the fruit. In pepos (such as watermelon, cantelope, honeydew, cucumber and squash) the equivalent tissue for expression is most likely the inner edible portions, whereas in legumes (such as peas, green beans, soybeans) the equivalent tissue is the seed pod.

Of particular interest for the subject invention is a fruit specific transcriptional initiation region (promoter) which encodes a protein described as 2A11 in the Experimental section. The promoter was obtained by screening cDNA clones made from ripe fruit using cNA probes made from ripe fruit, green fruit, and leaf mRNA. Clones were selected having more intense hybridization with the fruit DNAs as contrasted with the leaf cDNAs. The screening was repeated to identify a particular cDNA referred to as 2A11. The 2A11 cDNA was then used for screening RNA from root, stem, leaf, and seven stages of fruit development after the mRNA was sized on gels. The screening demonstrated that the particular message was present throughout the seven stages of fruit development. The mRNA complementary to the specific cDNA was absent in other tissues which were tested. The cDNA was then used for screening a genomic library and a fragment selected which hybridized to the subject cDNA. The 5' and 3' non-coding regions were isolated and manipulated for insertion of a foreign sequence to be transcribed under the regulation of the 2A11 promoter.

The cells which have been transformed may be grown into plants in accordance with conventional ways. See, for example, McCormick et al. *Plant Cell Reports* (1986) 5: 81–84. These plants may then be grown, and either pollinated with the same transformed strain or different strains, identifying the resulting hybrid having the desired phenotypic characteristic. Two or more generations may be grown to ensure that the subject phenotypic characteristic is stably maintained and inherited and then seeds harvested for use to provide fruits with the new phenotypic property.

A protein is provided having the sequence described in the Experimental Section designated as 2A11. This protein could be a storage protein and be useful in enhancing sulfur containing amino acids (cysteine and methionine) in the diet. It can be obtained in substantially pure form by providing for expression in prokaryotes or eukaryotes, e.g., yeast by inserting the open reading frame into an expression cassette containing a transcriptional initiation region. A variety of expression cassettes are commercially available or have been described in the literature. See, for example, U.S. Pat. Nos. 4,532,207; 4,546,082; 4,551,433; and 4,559,302. The product, if intracellular, may be isolated by lysing of the cells and purification of the protein using electrophoresis, affinity chromatography, HPLC extraction, or the like. The product may be isolated in substantially pure form free of other plant products, generally having at least about 95% purity, usually at least about 99% purity.

The following examples are offered by way of illustration and not by limitation.

EXPERIMENTAL

*E. coli* strain PCGN1299/71-18 was deposited at the A.T.C.C. on May 27, 1987 and given Accession No. 67408.

EXAMPLE 1

Construction of Tomato Ripe Fruit cDNA Bank and Screening for Fruit-Specific Clones Tomato plants (*Lycopersicon esculentum* cv UC82B) were grown under greenhouse conditions. Poly(A)+ RNA was isolated as described by Mansson et al., *Mol. Gen. Genet.* (1985) 200: 356–361. The synthesis of cDNA from poly(A)+ RNA prepared from ripe fruit, cloning into the PstI site of the plasmid pUC9 and transformation into an *E. coli* vector were all as described in Mansson et al., *Mol. Gen. Genet.* (1985) 200: 356–361.

Library Screening

Two thousand recombinant clones were screened by colony hybridization with radiolabeled cDNA made from tomato red fruit mRNA, immature green fruit mRNA, and leaf mRNA. Bacterial colonies immobilized onto GeneScreen Plus filters (New England Nuclear), were denatured in 1.5M NaCl in 0.5M NaOH, then neutralized in 1.5M NaCl in 0.5M Tris-HCl pH 8, and allowed to air dry. Hybridization, washing and autoradiography were all performed as described in Maniatis et al., Molecular Cloning: A Laboratory Manual (1982) Cold Spring Harbor, N.Y.

Sixty-five clones were selected which had more intense hybridization signals with fruit cDNA than with leaf cDNA and therefore appeared to be under-represented in the leaf mRNA population relative to the fruit population. Replicate slot blot filters were prepared using purified DNA from the selected clones and hybridized with radioactive cDNA from leaf, green fruit, and red fruit as before. This allowed selection of cDNA clone 2A11, also referred to as pCGN1299 which is on at high levels in both the fruit stages (red and green) and off in the leaf.

EXAMPLE 2

Analysis of Clones

Synthesis of RNA Probes

The cDNA insert of pCGN1299 was excised as an EcoRI to HindIII fragment of approximately 600 bp (as measured on an agarose gel), and subcloned into the Riboprobe vector pGEM1 (Promega Biotec), creating pCGN488. $^{32}$P-labeled transcripts made from each strand of the pCGN488 insert using either SP6 or T7 polymerase were used as probes in separate Northern blots containing mRNA from leaf, immature green and mature red fruits. The RNA transcript from the SP6 promoter did not hybridize to the tomato mRNA. However, the transcript from the T7 promoter hybridized to an mRNA of approximately 700nt in length from the green fruit and the red fruit but not to mRNA from tomato leaf. The direction of transcription of the corresponding mRNA was thus determined.

The tissue specificity of the pCGN1299 cDNA was demonstrated as follows. RNA from root, stem, leaf, and seven stages of fruit development (immature green, mature green, breaker, turning, pink, light red, and red) was sized on formaldehyde/agarose gels according to the method described by Maniatis et al., (1982), immobilized on nitrocellulose and hybridized to $^{32}$P-labeled RNA which was synthesized in vitro from pCGN488 using T7 polymerase. Each lane contained 100ng of polyA+ RNA except for two lanes (pink and light red lanes) which contained 10 μg of total RNA. The Northern analysis of mRNA from root, stem, leaf, and various stages of fruit development indicated that pCGN1299 cDNA was expressed in all stages of fruit development from the early stages immediately after anthesis to red ripe fruit. No mRNA hybridizing to pCGN1299 was found in leaf, stem, or root tissue. The size of the mRNA species hybridizing to the pCGN488 probe was approximately 700nt.

Message abundance corresponding to the pCGN1299 cDNA was determined by comparing the hybridization intensity of a known amount of RNA synthesized in vitro from pCGN488 using SP6 polymerase to mRNA from red tomato fruit in a Northern blot. The $^{32}$P-labeled transcript from pCGN488 synthesized in vitro using T7 polymerase was used as a probe. The Northern analysis was compared to standards which indicated that the pCGN1299 cDNA represents an abundant mRNA class in tomato fruit, being approximately 1% of the message.

EXAMPLE 3

Sequencing of pCGN1299 and pCGN1298 cDNA Clones

DNA Sequencing

The polyA+ sequence was missing from pCGN1299 cDNA. A longer cDNA clone, pCGN1298, therefore was identified by its hybridization with the pCGN488 probe. The complete DNA sequence of the two cDNA inserts was determined using both Maxam-Gilbert and the Sanger dideoxy techniques and is as follows. The sequence of pCGN1298 contains additional sequences at both the 5' and 3' end compared to pCGN1299. The sequences are identical over the region that the two clones have in common.

Amino Acid Sequence

The pCGN1299 cDNA sequence was translated in three frames. The longest open reading frame (which starts from the first ATG) is indicated. Both pCGN1299 and pCGN1298 have an open reading frame which encodes a 96 amino acid polypeptide as follows. The protein has a hydrophobic N-terminus which may indicate a leader peptide for protein targeting. The hydrophobicity profile was calculated using the Hopp and Woods, (*Proc. Natl. Acad. Sci. USA* (1981) 78: 3824–3828) algorithm. Residues 10–23 have an extremely hydrophobic region. The following is a comparison of the 2A11 protein sequence to pea albumin 1b (PA1b) and a number of other low molecular weight abundant proteins from plants.

Comparison of 2A11 to pea storage proteins and other abundant storage proteins. 2A11 (residues 33–46) comparison with PA1b and the reactive site sequences of some protease inhibitors, PA1b (residues 6–23), chick pea inhibitor (residues 11–23), lima bean inhibitor (residues 23–35), human α1-anti-trypsin reactive site peptide. Arrow indicates the reactive site. b, comparison of the NH$_2$-terminal sequence of 2A11 PA1b with the NH$_2$ termini of a range of seed proteins. Data modified, deletion introduced to maximize homology; conserved residues are boxed. The sequences are from the following sources: barley chloroform/methanol-soluble protein d and wheat albumin, wheat α-amylase inhibitor 0.28, millet bifunctional inhibitor, castor bean 2 S small subunit, napin small subunit. The sulfur-rich composites of the fruit specific protein is similar to a pea storage protein which has recently been described (See Higgins et al., *J. Biol. Chem* (1986) 261: 11124–11130, for references to the individual peptides). This may indicate a storage role for this fruit specific protein abundant species.

EXAMPLE 4

Screening Genomic Library for Genomic Clones

Southern Hybridization

Southern analysis was performed as described by Maniatis et al., 1982. Total tomato DNA from cultivar UC82B was digested with EcoRI or HindIII, separated by agarose gel electrophoresis and transferred to nitrocellulose. Southern hybridization was performed using a $^{32}$P-labeled probe produced by nick translation of pCGN488 (Maniatis, et al., 1982). The simple hybridization pattern indicated that the gene encoding pCGN1299 cDNA was present in a few or perhaps even one copy in a tomato genome.

Isolation of a Genomic Clone

A genomic library established in Charon35/Sau3A constructed from DNA of the tomato cultivar VFNT-Cherry was screened using the [$^{32}$P]-RNA from cDNA clone pCGN488 as a probe. A genomic clone containing approximately 12.5 kb of sequence from the tomato genome was isolated. The region which hybridizes to a PCGN488 probe spans an XBaI restriction site which was found in the cDNA sequence and includes the transcriptional initiation region designated 2A11.

Sequence of Genomic Clone

The DNA sequence of the genomic clone was determined by Sanger dideoxy techniques and is as shown above. The sequence of the genomic clone is identical to the pCGN1299 cDNA clone over the region they have in common.

Subcloning

The region surrounding the XbaI restriction site, approximately 2.4 kb in the 5' direction and approximately 2.1 kb in the 3'direction was subcloned to provide an expression cassette. The 5'XhoI to XbaI fragment and the 3' XbaI to EcoRI fragment from the 2A11 genomic clone were inserted via XhoI linkers into a pUC-derived chloromphenicol plasmid containing a unique XhoI site and no XbaI site. This promoter cassette plasmid is called pCGN1273.

EXAMPLE 5

Construction of Fruit-Specific Antisense Cassette

Insertion of Antisense Fragment

The 2A11 genomic fragment was tagged with PG antisense sequences by insertion of PG into the unique XbaI site of the pCGN1273 promoter cassette in the antisense orientation. The inserted sequences increased the size of the mRNA over the endogenous transcript, and thus the expression pattern of the construct could be compared to the endogenous gene by a single Northern hybridization in a manner analogous to the detection of a tuber-specific potato gene described by Eckes, et al., *Mol. Gen. Genet.* 1986 205: 14-22.

EXAMPLE 6

Insertion of Tagged Genomic Construction Into Agrobacterium Binary Vectors

The tagged genomic construction is excised using the flanking XhoI restriction enzyme sites and is cloned into the unique SalI site of the binary plasmid pCGN783 containing a plant kanamycin resistance marker between the left and right borders to provide plasmid pCGN1269.

This plasmid binary vector in *E. coli* C2110 is conjugated into *Agrobacterium tumefaciens* containing a disarmed Ti plasmid capable of transferring the polygalacturonase anti-sense cassette and the kanamycin resistance cassette into the plant host genome.

The Agrobacterium system which is employed is *A. tumefaciens* PC2760 (G. Ooms et al., *Plasmid* (1982) 7: 15-29; Hoekema et al., *Nature* (1983) 303: 179-181; European Patent Application 84-200239.6, 2424183).

Figure 3:
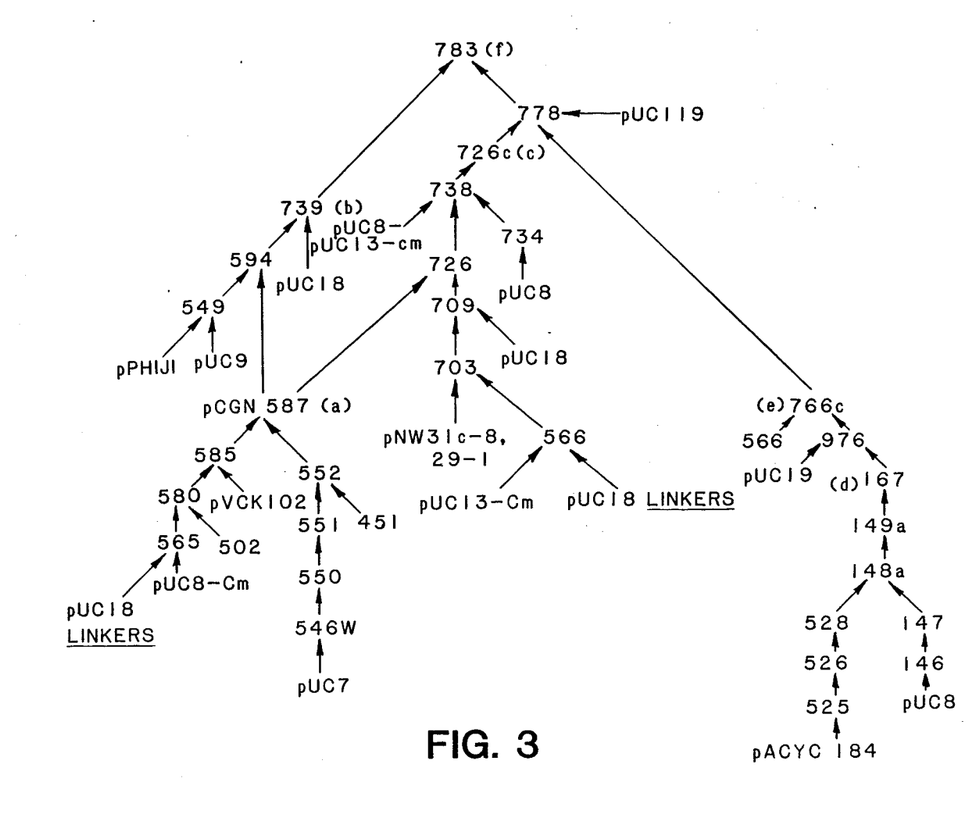
FIG. 3 shows a schematic of the construction of pCGN783.

Construction of pCGN783 pCGN783 is a binary plasmid containing the left and right T-DNA borders of *Agrobacterium tumefaciens* octopine Ti-plasmid pTiA6 (Currier and Nester *J. Bacteriol.* (1976) 126: 157-165) the gentamicin resistance gene of pPH1J1 (Hirsch et al., *Plasmid* (1984) 12: 139-141), the 35S promoter of cauliflower mosaic virus (CaMV) (Gardner et al., *Nucleic Acid Res.* (1981) 9: 1871-1880); the kanamycin resistance gene of Tn5 (Jorgensen, *Mol. Gen.* (1979) 177: 65); and the 3' region from transcript 7 of pTiA6 (Currier and Nester, supra (1976)).

Construction of pCGN793 (Binary Vector)

To obtain the gentamicin resistance marker, the resistance gene was isolated from a 3.1 kb EcoRI-PstI fragment of pPHIJI (Hirsch et al., *Plasmid* (1984) 12: 139-141) and cloned into pUC9 (Vieira et al., *Gene* (1982) 19: 259-268) yielding pCGN549.

The pCGN549 HindIII-BamHI fragment containing the gentamicin resistance gene replaced the HindIII-BglII fragment of pCGN587 (for construction, see infra) creating pCGN594.

The pCGN594.HindIII-BamHI region which contains an ocs-kanamycin-ocs fragment was replaced with the HindIII-BamHI polylinker region from pUC18 (Yanisch-Perron, *Gene* (1985) 33: 103-119) to make pCGN739.

Construction of 726c (1 ATG-Kanamycin-3' region)

pCGN566 contains the EcoRi-HindIII linker of pUC18 (Yanisch-Perron, ibid) inserted into the EcoRI-HindIII sites of pUC13-Cm (K. Buckley, Ph.D. Thesis, University of California, San Diego, 1985). The HindIII-BglII fragment of pNW31c-8, 29-1 (Thomashow et al., *Cell* (1980) 19: 729) containing ORF1 and 2 (Barker et al., *Plant Mol. Biol.* (1984) 2: 335-350) was subcloned into the HindIII-BamHI sites of pCGN566 producing pCGN703.

The Sau3A fragment of pCGN703 containing the 3' region of transcript 7 from pTiA6 (corresponding to bases 2396-2960 of pTi15955 (Barker et al., supra (1984)) was subcloned into the BamHI site of pUC18 (Yanisch-Perron et al., supra (1985)) producing pCGN709.

The EcoRI-SmaI polylinker region of pCGN709 was replaced with the EcoRI-SmaI fragment from pCGN587 (for production see infra) which contains the kanamycin resistance gene (APH3'II) producing pCGN726.

The EcoRI-SalI fragment of pCGN726 plus the BglII-SalI sites of pUC8-pUC13-cm (chlorophenical resistant, K. Buckley, Ph.D. Thesis, University of California, San Diego, 1985) producing pCGN738. To construct pCGN734, the HindIII-SphI fragment of pTiA6 corresponding to bases 3390-3241 (barker et al. (1983), supra) was cloned into the site of M13mp19 (Norrander et al., *Gene* (1983) 26: 101-106). Using an oligonucleotide corresponding to bases 3287 to 3300, DNA synthesis was primed from this template. Following S1 nuclease treatment and HindIII digestion, the resulting fragment was cloned into the HindIII-SmaI site of pUC19 (Yanisch-Perron et al., supra (1985)). The resulting EcoRI to HindIII fragment of pTiA6 (corresponding to bases 3390-4494) into the EcoRI site of pUC8 (Vieira and Messing, supra (1982) resulting in pCGN734. pCGN726c is derived from pCGN738 by deleting the 900 bp EcoRI-EcoRI fragment.

Construction of pCGN766c (35S promoter - 3' region)

The HindIII-BamHI fragment of pCGN167 (for construction see infra) containing the CaMV-35S promoter, 1 ATG-kanamycin gene and the BamHI fragment 19 of pTiA6 was cloned into the BamHI-HindIII sites of pUC19 (Norrander et al., supra (1985; Yanisch-Perron et al., supra (1985)) creating pCGN976.

The 35S promoter and 3' region from transcript 7 was developed by inserting a 0.7 kB HindIII-EcoRI fragment of pCGN976 (35S promoter) and the 0.5 kb EcoRI-SalI fragment of pCGN709 (transcript 7: 3' for construction see supra) into the HindIII-SalI sites of pCGN566 creating pCGN766c.

Final Construction of pCGN783

The 0.7 kb HindIII-EcoRI fragment of pCGN766c (CaMV-35S promoter) was ligated to the 1.5 kb EcoRI-SalI fragment of pCGN726c (1-ATG-KAN-3' region) into the HindIII-SalI sites of pUC119 (J. Vieira, Rutgers University, New Jersey) to produce pCGN778.

The 2.2 kb region of pCGN778, HindIII-SalI fragment containing the CaMV 35S promoter (1-ATG-KAN-3' region) replaced the HindIII-SalI polylinker region of pCGN739 to produce pCGN783.

pCGN587 was prepared as follows: The HindIII-SmaI fragment of Tn5 containing the entire structural gene for APH3'II (Jorgensen et al., Mol. Gen. (1979) 177: 65), was cloned into pUC8 (Vieira and Messing, Gene (1982) 19: 259), converting the fragment into a HindIII-EcoRI fragment, since there is an EcoRI site immediately adjacent to the SmaI site. The PstI-EcoRI fragment containing the 3' portion of the APH3'II gene was then combined with an EcoRI-BamHI-SalI-PstI linker into the EcoRI site of pUC7 (pCGN546W). Since this construct does not confer kanamycin resistance, Kanamycin resistance was obtained by inserting the BglI-PstI fragment of the APH3'II gene into the BamHI-PstI site (pCGN546X). This procedure reassembles the APH3'II gene, so that EcoRI sites flank the gene. An ATG codon was upstream from and out of reading frame with the ATG initiation codon of APH3'II. The undesired ATG was avoided by inserting a Sau3A-PstI fragment from the 5' end of APH3'II, which fragment lacks the superfluous ATG, into the BamHI-PstI site of pCGN546W to provide plasmid pCGN550. The EcoRI fragment of pCGN550 containing the APH3'II gene was then cloned into the EcoRI site of pUC8-pUC13 (K. Buckley supra (1985)) to give pCGN551.

Each of the EcoRI fragments containing the APH-3'II gene was then cloned into the unique EcoRI site of pCGN451, which contains an octopine synthase cassette for expression to provide pCGN548 (2ATG)) and pCGN552 (1ATG). The plasmid pCGN451 having the ocs 5' and the ocs 3' in the proper orientation was digested with EcoRI and the EcoRI fragment from pCGN551 containing the intact kanamycin resistance gene inserted with EcoRI site to provide pCGN552 having the kanamycin resistance gene in the proper orientation.

This ocs/KAN gene was used to provide a selectable marker for the trans type binary vector pCGN587.

The 5' portion of the engineered octopine synthase promoter cassette consists of pTiA6 DNA from the XhoI at bp 15208-13644 (Barker et al., supra (1983)), which also contains the T-DNA boundary sequence (border) implicated in T-DNA transfer. In the plasmid pCGN587, the osc/KAN gene from pCGN552 provides a selectable marker as well as the right border. The left boundary region was first cloned in M13mp9 as a HindIII-SmaI piece (pCGN502) (base pairs 602-2212) and recloned as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglI fragment of pVCK102 (Knauf and Nester, Plasmid (1982) 8: 45), creating pCGN585. By replacing the smaller SalI fragment of pCGN585 with the XhoI fragment from pCGN552 containing the ocs/KAN gene, pCGN587 was obtained.

To construct pCGN167, the AluI fragment of CaMV (bp 7144–7735) (Gardner et al., Nucl. Acids. Res. (1981) 9: 2871–2888) was obtained by digestion with AluI and cloned into the HincII site of M13mp7 (Vieira, Gene (1982) 19: 259) to create C614. An EcoRI digest of C614 produced the EcoRI fragment from C614 containing the 35S promoter which was cloned into the EcoRI site of pUC8 (Vieira et al., Gene (1982) 19: 259) to produce pCGN146.

To trim the promoter region, the BglII site (bp 7670) was treated with BglII and Bal31 and subsequently a BglII linker was attached to the Bal31 treated DNA to produce pCGN147.

pCGN148a containing promoter region, selectable marker (KAN with 2 ATGs) and 3' region was prepared by digesting pCGN528 (see below) with BglII and inserting the BAMHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., Mol. Gen. (1979) 177: 65) with HindIII-BamHI and inserting the HindIII-BamHI fragment containing the kanamycin gene into the HindIII-BamHI sites in the tetracycline gene of pACYC184 (Chang and Cohen, J. Bacteriol. (1978) 134: 1141–1156). pCGN526 was made by inserting the BamHI fragment 19 of pTiA6 (Thomashow et al., Cell (1980) 19: 729–739) into the BamHI site of pCGN525. pCGN528 was obtained by deleting the small XhoI fragment from pCGN526 by digesting with XhoI and religating.

pCGN149a was made by cloning the BamHI kanamycin gene fragment from pMB9KanXXI into the BamHI site of pCGN148a.

pMB9KanXXI is a pUC4K variant (Vieira and Messing, Gene (1982) 19: 259–268) which has the XhoI site missing but contains a functional kanamycin gene from Tn903 to allow for efficient selection in Agrobacterium.

pCGN194a was digested with BglII and SphI. This small BglII-SphI fragment of pCGN149a was replaced with the BamHI-SphI fragment from MI (see below) isolated by digestion with BamHI and SphI. This produces pCGN167, a construct containing a full length CaMV promoter, 1 ATG-kanamycin gene, 3' end and the bacterial Tn903-type kanamycin gene. MI is an EcoRI fragment from pCGN550 (see construction of pCGN587) and was cloned into the EcoRI cloning site in the 1 ATG-kanamycin gene was proximal to the polylinker region of M13mp9. See copending application Serial No. 920,579, filed Oct. 17, 1986, which disclosure is incorporated herein by reference.

EXAMPLE 7

Transfer of Genomic Construction to Tomato via Cocultivation

Substantially sterile tomato cotyledon tissue is obtained from seedlings which had been grown at 24° C., with a 16 hr/8 hr day/night cycle in 100×25 mm petri dishes containing Murashige-Skoog salt medium and 0.8% agar (pH 6.0). Any tomato species may be used, however, here the inbred breeding line was UC82B, available from the Department of Vegetable Crops, University of California, Davis, CA 95616. The cotyledons are cut into three sections and the middle placed onto feeder plates for a 24-hour preincubation. The feeder plates are prepared by pipetting 0.5 ml of a tobacco suspension culture (~10⁶ cells/ml) onto 0.8% agar medium, containing Murashige minimal organic medium (K.C. Biologicals), 2,4-D (0.1 mg/L), kinetin (1 mg/L), thiamine (0.9 mg/L) and potassium acid phosphate (200 mg/L, pH 5.5). The feeder plates are prepared two days prior to use. A sterile 3 mm filter paper disk containing feeder medium is placed on top of the tobacco cells after the suspension cells are grown for two days.

Following the preincubation period, the middle one third of the cotyledon sections are placed into a liquid MG/L broth culture (1–5 ml) of the *Agrobacterium tumefaciens* strain. The binary plasmid pCGN1269 is transferred to *A. tumefaciens* strain 2760 by conjugation or by transformation selecting for Gentamicin resistance encoded by the plasmid pCGN1269. The cotyledon sections are cocultivated with the bacteria for 48 hrs on the feeder plates and then transferred to regeneration medium containing 500 mg/L carbenicillin and 100 mg/L kanamycin. The regeneration medium is a K.C. Biologicals Murashige-Skoog salts medium with zeatin (2 mg/L) myo-inositol (100 mg/L), sucrose (20 g/L), Nitsch vitamins and containing 0.8% agar (pH 6.0). In 2 to 3 weeks, shoots are observed to develop. When the shoots are approximately 1.25 cm, they are excised and transferred to a Murashige and Skoog medium containing carbenicillin (500 mg/L) and kanamycin (50 mg/L) for rooting. Roots develop within 10–12 days.

Shoots which develop and subsequently root on media containing the kanamycin are tested for APH enzyme.

An aminoglycoside phosphotransferase enzyme (APH 3′II) assay is conducted on putative transformed tomato plants and shoots. APH 3′II confers resistance to kanamycin and neomycin. APH 3′II activity is assayed (Reiss et al., *Gene* (1984) 30: 211–218) employing electrophoretic separation of the enzyme from other interfering proteins and detection of its enzymatic activity by situ phosphorylation of kanamycin. Both kanamycin and [γ-³²P] ATP act as substrates and are embedded in an agarose gel which is placed on top of the polyacrylamide gel containing the proteins. After the enzymatic reaction, the phosphorylated kanamycin is transferred to P-81 phosphocellulose ion exchange paper and the radiolabeled kanamycin is finally visualized by autoradiography. The Reiss et al. method is modified in the final washing of the P-81 ion exchange paper by rinsing in 0.1 mg/ml of proteinase K.

The above results demonstrate the ability to identify inducible regulatory sequences in a plant genome, isolate the sequences and manipulate them. In this way, the production of transcription cassettes and expression cassettes can be produced which allow for differentiated cell production of the desired product. Thus, the phenotype of a particular plant part may be modified, without requiring that the regulated product be produced in all tissues, which may result in various adverse effects on the growth, health, and production capabilities of the plant. Particularly, fruit specific transcription initiation capability is provided for modifying the phenotypic properties of a variety of fruits to enhance properties of interest such as processing, organoleptin properties, storage, yield, or the like.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising in the direction of transcription, a tomato 2All transcriptional initiation region joined to a DNA sequence of interest, wherein said DNA sequence of interest is other than the wild-type sequence and is under the transcriptional regulation of said 2All initiation region and a transcriptional termination region.

2. A DNA construct according to claim 1, wherein said DNA sequence of interest is a sequence complementary to a native plant transcript.

3. A DNA construct according to claim 1, wherein said DNA sequence of interest is an open reading frame encoding an amino acid sequence of interest.

4. A DNA construct for integration into a plant genome comprising at least the right T-DNA border joined to a DNA construct according to claim 1.

5. A DNA construct comprising in the direction of transcription, a tomato 2All transcriptional initiation region joined to a DNA sequence of interest, wherein said DNA sequence is other than the wild-type sequence and comprises a unique restriction site for insertion of a second DNA sequence of interest to be under the transcriptional regulation of said 2All initiation region, and a transcriptional termination region.

6. A DNA construct for integration into a plant genome comprising at least the right T-DNA border joined to a DNA construct according to claim 5.

7. A DNA vector comprising a broad spectrum prokaryotic replication system and a DNA construct according to claim 1.

8. A DNA vector comprising a broad spectrum prokaryotic replication system and a DNA construct according to claim 5.

9. A method for modifying the phenotype of tomato fruit said method comprising:
   transforming a tomato plant cell with a DNA construct under genomic integration conditions, wherein said DNA construct comprises in the direction of transcription, a tomato 2All transcriptional initiation region jointed to a DNA sequence other than the wild-type sequence and capable of modifying the phenotype of fruit cells upon transcription, wherein said DNA sequence is under the transcriptional regulation of said initiation region and a transcriptional termination region, whereby said DNA construct becomes integrated into the genome of said tomato plant cell;
   regenerating a plant from said transformed tomato plant cell; and
   growing said plant to produce tomato fruit of the modified phenotype.

10. A plant cell comprising a DNA construct according to claim 1.

11. A plant cell comprising a DNA construct according to claim 5.

12. Tomato fruit comprising a DNA construct comprising in the direction of transcription, a tomato 2All transcriptional initiation region joined to a DNA sequence of interest, wherein said DNA sequence is other than the wild-type sequence and is under the transcriptional regulation of said 2All initiation region, and a transcriptional termination region.

13. A tomato plant comprising:
a DNA construct comprising in the direction of transcription, a tomato 2All transcriptional initiation region joined to a DNA sequence of interest, wherein said DNA sequence is other than the wild-type sequence and is under the transcriptional regulation of said 2All initiation region, and a transcriptional termination region.

14. A tomato plant comprising:
a DNA construct comprising in the direction of transcription, a tomato 2All transcriptional initiation region joined to a DNA sequence of interest, wherein said DNA sequence is other than the wild-type sequence and comprises a unique restriction site for insertion of a second DNA sequence of interest to be under the transcriptional regulation of said 2All initiation region, and a transcriptional termination region.

* * * * *